United States Patent [19]
DeSimone

[11] 3,960,923
[45] June 1, 1976

[54] PROCESS FOR THE PREPARATION OF α,β-UNSATURATED NITRILES
[75] Inventor: Robert S. DeSimone, Willingboro, N.J.
[73] Assignee: Rhodia, Inc., New York, N.Y.
[22] Filed: Dec. 3, 1973
[21] Appl. No.: 421,200

[52] U.S. Cl............................ 260/465.9; 252/522; 260/464
[51] Int. Cl.² .................................. C07C 120/00
[58] Field of Search.................... 260/464, 465.9

[56] References Cited
UNITED STATES PATENTS
3,852,321  12/1974  Babler................................ 260/464
3,869,493  3/1975  Bozzato et al. .................... 260/464

FOREIGN PATENTS OR APPLICATIONS
2,135,666  1/1973  Germany ............................ 260/464
2,302,219  8/1973  Germany ......................... 260/465.3

OTHER PUBLICATIONS
Arpe, et al., Angew. Chem., Int. Ed. Engl. Aug. 1972, vol. 11(8), p. 722.

Primary Examiner—Joseph P. Brust

[57] ABSTRACT

A process is provided for the preparation of α,β-unsaturated nitriles by reaction of a ketone and acetonitrile in the presence of a base. Many of the α,β-unsaturated nitriles thus prepared are novel compounds, and all are useful in perfumery. Perfume compositions also are provided, containing effective amounts of such α,β-unsaturated nitriles.

28 Claims, No Drawings

PROCESS FOR THE PREPARATION OF α,β-UNSATURATED NITRILES

Mitchell and Blumenthal U.S. Pat. No. 3,655,722 describe a method for the preparation and isolation of a variety of 7-methyl-2,6-octadienenitriles by condensation of cyanoacetic acid with 2-methyl-2-heptene-6-one in the presence of an amine or an acid addition salt of an amine at from about 40° to about 180°C. A mixture of nitriles is produced, and these mixtures are useful in perfume compositions. Among the compounds prepared are neronitrile and geranonitrile. The perfume compositions can be used alone or blended into soaps, detergents, space sprays, cosmetics, and the like.

When prepared by this method, the unsaturated nitriles are expensive, because of low yields. The direct yield for the preparation of geranonitrile and neronitrile is about 22 percent, while the true yield, after recovery of unreacted methylheptenone, is about 40 percent.

Arpe and Leupold, *Angew. Chem.* 84 767 (1972), *Angew. Chem. Internat. Edit.* 11 722 (1972), German Offenlegungsschrift No. 2,135,666 laid open Jan. 25, 1973, describe the reaction of acetonitrile with ketones such as cyclohexanone to prepare cyclohexylidene acetonitrile using an alkali metal alcoholate of a high boiling alcohol having a boiling point higher than the boiling point of the highest boiling component of the reaction mixture, such as n-octanol. They state that:

"With alkali ethoxide the reaction comes to a standstill after 5–10% conversion since the ethanol formed in the hydrolysis of the alcoholate distills off. The basicity of the remaining alkali hydroxide is insufficient for abstraction of H+ from the acetonitrile."

Water is separated by azeotropic distillation as the reaction proceeds and a 70 percent yield is claimed in the case of cyclohexylidene acetonitrile.

In accordance with the invention, a process is provided for preparing α,β-unsaturated nitriles, starting with inexpensive reagents. High yields are obtained, with the result that the process of the invention makes it possible to prepare nitriles such as geranonitrile and neronitrile at low cost.

In accordance with the invention, a ketone is reacted with acetonitrile in the presence of a base selected from the group consisting of alkali metal hydroxides, barium hydroxide, alkali metal lower alcoholate and quaternary ammonium hydroxides. The acetonitrile inserts a =CHCN group at the keto group of the ketone, displacing the oxygen atom, with the formation of an unsaturated bond at the α,β-position between the methylene carbon of the acetonitrile and the keto carbon of the ketone. The reaction accordingly proceeds as follows:

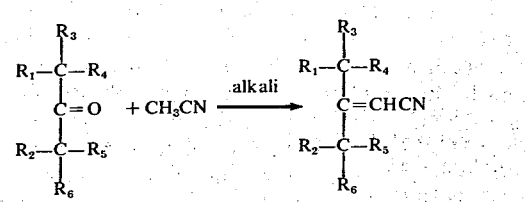

In the above formula, $R_1$ and $R_2$ are selected from the group consisting of hydrogen and alkyl and alkenyl groups having from one to about 20 carbon atoms, and $R_3$, $R_4$, $R_5$, and $R_6$ are selected from the group consisting of hydrogen and alkyl groups having from one to about 20 carbon atoms.

It will be apparent that when a saturated ketone is used, the reaction produce is a monoethylenically α,β-unsaturated nitrile, while if an unsaturated monoethylenic ketone is used, the reaction product is a dienic α,β-unsaturated nitrile.

In the preparation of geranylo-nerylo nitriles, the starting ketone is methylheptenone:

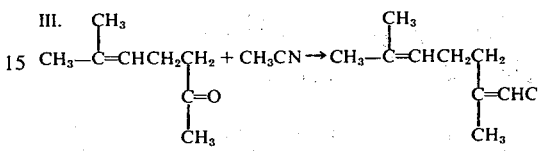

or

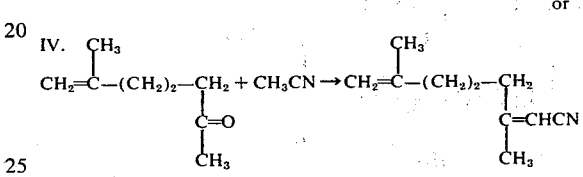

Other ketones which can be used include 3,6-dimethyl-5-hepten-2-one, 3,6-dimethyl hepten-2-one, 7-methyl-6-octen-3-one, 7-methylocten-3-one, 6-methyl-5-hepten-2-one, 6-methylhepten-2-one, 4,7-dimethyl-6-octen-3-one, 4,7-dimethylocten-3-one, 2,7-dimethyl-6-octen-3-one, 2,7-dimethyl octen-3-one, cyclohexanone, cyclopentanone, cycloheptanone, cyclohexenone, cyclopentenone, cycloheptenone, 2-prenyl-cyclohexanone, and 2-prenyl-cyclopentanone. Additional ketones include:

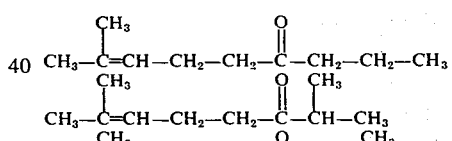
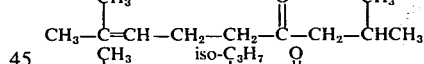
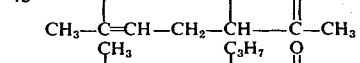
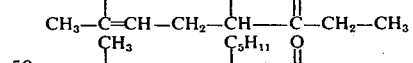
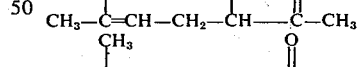
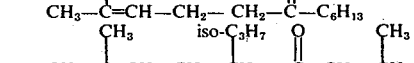
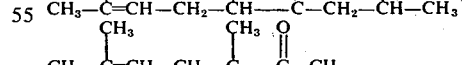
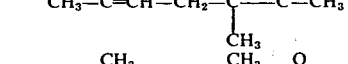
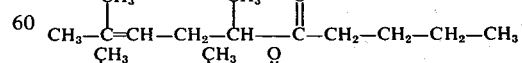
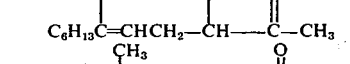
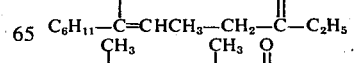
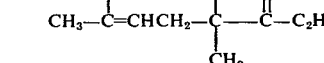

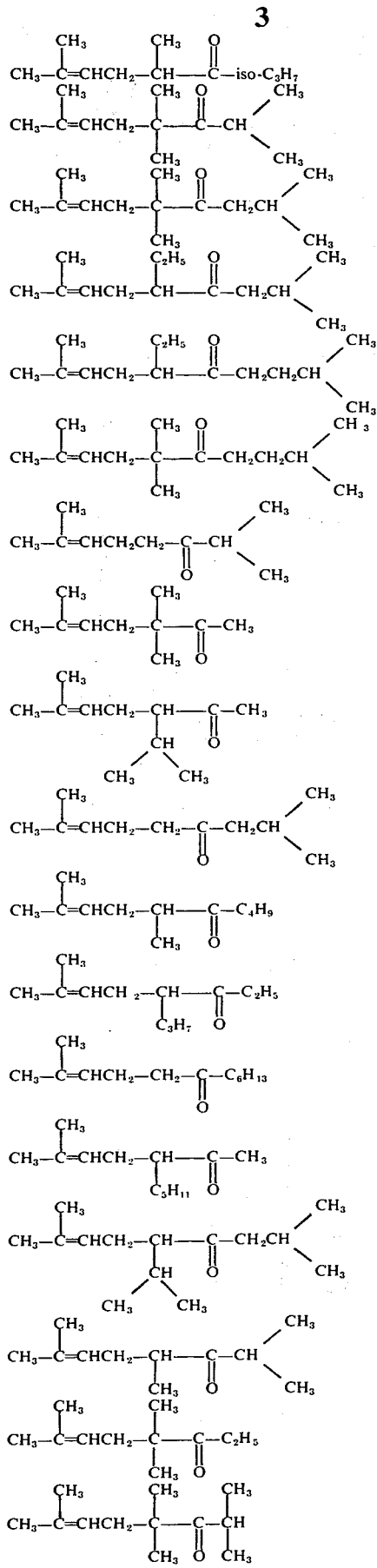
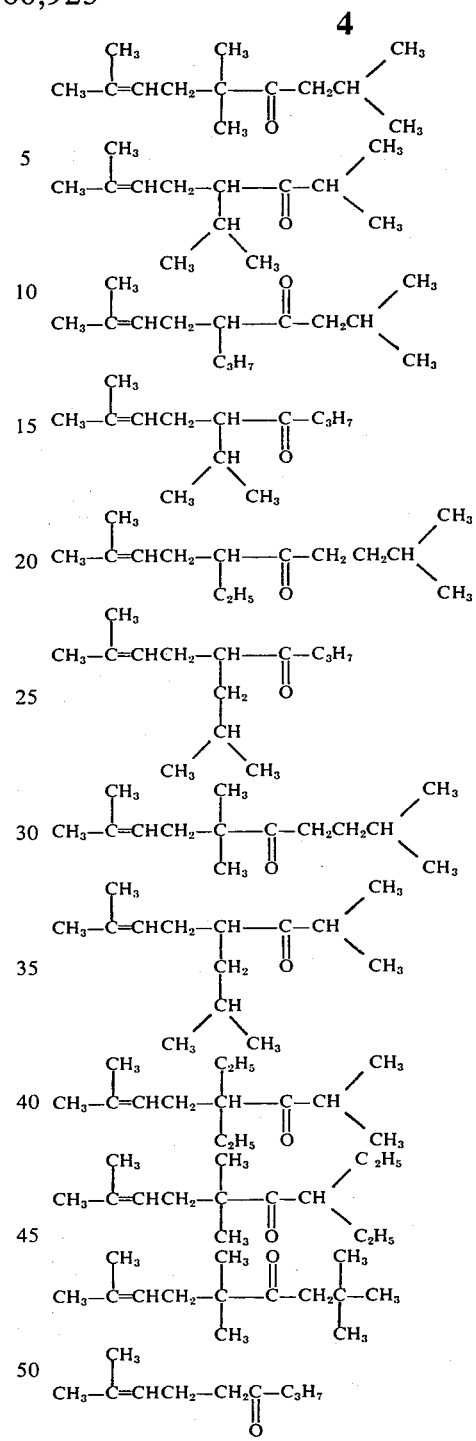

The reaction proceeds with stoichiometric ratios of ketone and acetonitrile. However, an excess of either reagent can be used, if desired. If excess ketone or acetonitrile is used, it can be recovered at the end of the reaction, and recycled.

Any strong alkali can be used. The alkali metal hydroxides, such as sodium and potassium hydroxide, and the alkali metal alkoxides of the lower aliphatic alcohols having from one to about four carbon atoms, such as potassium tertiary butylate, sodium propylate, potassium isopropylate, sodium ethylate, potassium methylate, sodium butylate, potassium isobutylate, potassium butylate, and sodium isopropylate, are preferred. However, barium hydroxide also can be used.

Quaternary ammonium hydroxides which are known to be quite strong bases also can be used. These have the general formula:

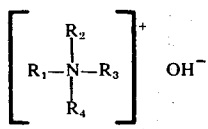

wherein $R_1$, $R_2$, $R_3$ and $R_4$ are organic radicals which may bear substituents such as hydroxyl and are selected from the group consisting of alkyl, hydroxyalkyl, cycloalkyl and aryl (which may be substituted with alkyl, hydroxyalkyl, halogen) having from one to about 30 carbon atoms.

The alkali is not consumed in the course of the reaction. It acts only as a catalyst. Consequently the amount of alkali is in no way critical, and can be within the range from about 0.01 to about 10 moles per mole of ketone. Preferably, the amount of base is within the range from about 0.1 to about 5 moles per mole of ketone. Normally, there is no need to use more than one mole of alkali per mole of ketone.

It is advantageous to have the alkali in solution at least to a certain extent, in which event the reaction rate is increased. An organic solvent for the base, particularly barium hydroxide, can consequently be included in the reaction mixture, such as dimethyl sulfoxide or m-pyrrole. Such solvents activate the base, and it is more effective in their presence.

It is not, however, necessary to add an inert solvent. Acetonitrile can serve not only as a reagent but also as a solvent, and for this purpose can be used in excess. The presence of acetonitrile is additionally beneficial in that it can serve as a water trapping agent. Water generated during the course of reaction is captured through a base-catalysed hydrolysis of acetonitrile to form acetamide.

Other water trapping agents such as molecular sieves may also be used.

It may be also advantageous to add an external inert solvent which may or may not be a solvent for the base, but which forms an azeotrope with water, so that by azeotropic distillation water liberated in the course of the reaction can be removed. Such water can be, for example, caught under reflux in a water trap, and does not return to the reaction mixture. Suitable azeotropic solvents include toluene, benzene and xylene.

The reaction proceeds at room temperature, or slightly below. It is, however, accelerated by increasing the temperature. The maximum temperature is imposed by the temperature of decomposition of the $\alpha,\beta$-unsaturated nitrile. Usually, the reaction temperature does not exceed about 200°C., and can range to 20°C. or below. The preferred temperature is within the range from 50° to about 125°C.

The reaction can be carried out at atmospheric pressure. If, however, a volatile solvent is used, and a reaction temperature at or near its boiling point at atmospheric pressure, it may be desirable to conduct the reaction in a closed reactor, such as an autoclave, in order to maintain the solvent in the liquid phase in the reaction mixture, or under reflux.

The reaction can be completed within about 30 minutes, but in some cases, an extended time, to as much as 120 hours or more, may be needed. This is without disadvantage, since the $\alpha,\beta$-unsaturated nitrile is the final product, and disproportionation or transmutation of this product into other materials does not appear to take place. The reaction time can be kept short by increasing the reaction temperature, improving the efficiency of the agitation, and using a concentrated reaction mixture.

At the completion of the reaction, the reaction mixture can be treated with acid to neutralize the base. The reaction product can then be dissolved in an organic solvent for the reaction product, such as benzene, which is not miscible with the aqueous phase, and in this way separate the aqueous phase from the organic phase containing the reaction product. The aqueous phase can be extracted several times with the solvent, in order to maximize the recovery.

Alternatively, the reaction mixture can be washed with water to remove the majority of base and acetamide. The remaining organic phase is then washed with a dilute aqueous acid solution to ensure removal of all remaining traces of base. The same result may be achieved through filtration of a crude reaction mixture to remove the majority of base and acetamide, again using an acid wash to remove any remaining traces of base. The acid washed could be combined and cross-extracted with a low-boiling organic solvent to maximize the recovery of product.

The combined organic phases can then be concentrated to remove the solvent, preferably at reduced pressure and a low temperature, and then distilled at reduced pressure to separate the unreacted starting materials, including starting ketone and acetonitrile, from the $\alpha,\beta$-unsaturated nitrile. The unsaturated nitrile product may exist as a cis, trans mixture, where stereoisomers are possible, but separation of cis, trans isomers is not necessary.

The following Examples in the opinion of the inventor represent preferred embodiments of the invention.

EXAMPLE 1

A mixture of 40 g of sodium hydroxide (1 mole), 410 g of acetonitrile (10 moles), and 135 g of 3,6-dimethyl-5-hepten-2-one containing about 15% 7-methyl-6-octen-3-one, was heated to reflux at about 84°C. with mechanical stirring under a static nitrogen head for a total of 72 hours. The reaction mixture was then allowed to cool, and stirred into 550 g of 10% aqueous acetic acid to neutralize the base.

50 ml of benzene was added, the mixture shaken, and then allowed to seperate, whereupon the aqueous phase was removed. The aqueous phase was extracted twice with 50 ml portions of benzene, and twice with 25 ml portions of benzene, and the benzene fractions combined. The combined benzene solutions were concentrated at about 40 mm Hg to remove the benzene, and the residue was then distilled under a pressure of from 2 to 5 mm Hg at a head temperature from 50° to 130°C. and a pot temperature from 58° to 158°C. In this manner, there was obtained 111.6 g of the unreacted starting ketone, and 20.4 g of a mixture of 3,4,7-trimethyl-2,6-octadiene nitrile and 3-ethyl-7-methyl-2,6-octadiene nitrile. The direct yield of dienic nitrile was 13 percent, and the true yield was 75 percent.

This mixture of nitriles has a lemony-citrus fragrance reminiscent of citral, fresh, clean and crisp. Its radiant lively character is very attractive, and in tune with today's popular natural citrus types. A soupcon of a distinctive green note enhances its appeal. Intense power and persistence are important additional attributes.

In addition to use in citrus aroma compositions, such as orange, neroli, lemon and cologne, it is an excellent ingredient for lavender, fern, fir needle, moss, new-mown hay and stability and woodsy bouquets. It is effective in floral perfumes such as rose and lily of the valley, when incorporated at low levels. As much as 25 percent or more can be used in lemon fragrances, depending on the end use. The nitrile mixture has a very high stablity in alkaline and acid media, and is therefore useful in products such as detergent, soap, depilatory, permanent hair wave, and hair rinse compositions.

EXAMPLE 2

A mixture of 56 g of potassium hydroxide, one mole, 410 g of acetonitrile, 10 moles, and 135 g of 3,6-dimethyl-5-hepten-2-one, containing about 15% of 7-methyl-6-octen-3-one, was heated to reflux with mechanical stirring under a static nitrogen head for a total of 15 hours. After cooling, the reaction mixture was poured into 900 ml of 10% acetic acid with stirring to neutralize the base.

50 ml of benzene was then added, the mixture shaken, and then the benzene phase separated. The aqueous phase was extracted with 50 ml of benzene. The benzene phases were combined, and the benzene distilled off at about 40 mm Hg. The resulting oil was washed three times with 25 ml portions of 10% HCl, and each extract was cross-extracted four times with 10 ml portions of benzene.

The combined benzene phases were then distilled to remove benzene at about 40 mm Hg. The residual oil was distilled under from 1 to 5 mm Hg at a head temperature of from 50° to 121°C. and a pot temperature from 78° to 152°C. In this manner, there was obtained 11.2 g of the unreacted starting ketone, and 113.6 g of a mixture of 3,4,7-trimethyl-2,6-octadiene nitrile and 3-ethyl-7-methyl-2,6-octadiene nitrile. The direct yield was 72.3 percent, and the true yield 78.9 percent.

EXAMPLES 3 TO 23

A mixture of potassium hydroxide, 11.2 g, 0.2 mole, 82 g of acetonitrile, 2 moles, and 25.2 g of methyl heptenone was heated to reflux at 84°C. with mechanical stirring under a static nitrogen head for 4.5 hours. After cooling, the reaction mixture was stirred into 125 ml of aqueous acetic acid to neutralize the base. The mixture was then shaken with 25 ml of benzene, and the benzene phase separated. The benzene phase was washed twice with 10 ml of 10% hydrochloric acid, and the aqueous phases re-extracted three times in succession with 15 ml portions of benzene.

The benzene phases were combined, and the benzene removed under aspirator vacuum. Distillation of the residual oil was carried out at 4.5 to 0.8 mm Hg under a head temperature of from 80° to 95°C. and a pot temperature of from 94° to 164°C. In this manner, there was recovered 0.5 g of unreacted methyl heptenone and 16.9 g of geranonitrile. The direct yield was 56.8 percent, and the true yield 58.0 percent.

Using this procedure, the ketones set forth in Table I were reacted with acetonitrile, under the conditions given in the Table:

TABLE I

| Ex. No. | Ketone and Nitrile | Moles per mole of Ketone | | Temp °C | Time Hr | Direct Yield | True Yield | ← Relative %⁴ by glc → | |
|---|---|---|---|---|---|---|---|---|---|
| | | Acetonitrile | Catalyst | | | | | % starting ketone | % nitrile |
| 4 | 3,6-Dimethyl-5-hepten-2-one ↓ 3,4,7-Trimethyl-2,6-octadiene nitrile and 7-Methyl-6-octen-3-one ↓ 3-Ethyl-7-methyl-2,6-octadiene nitrile | 10 | 1.0 NaOH | 81 | 80 | 13.0 | 74.6 | 84.7 | 15.3 |
| 5 | | 10 | 4.0 NaOH | 85 | 35 | not worked up | | 81.4 | 18.6 |
| 6 | | 10 | 1.0 KOH | 88 | 16 | 75.4 | 84.4 | 10.8 | 89.2 |
| 7 | | 10 | 0.1 NaOCH₃ | 84–86 | 42.5 | not worked up | | 87.2 | 12.8 |
| 8 | | 10 | 0.1 KOH | 84–85 | 91 | 63.0 | 77.2 | 19.3 | 76.8 |
| 9 | | 10 | 1.0 NaOCH₃ | 82–83 | 45.3 | 63.5 | 66.4 | 5.2 | 91.5 |
| 10 | | 10 | 1.0 NaOCH₃³ | 76–77 | 45.5 | 49.5 | 68.2 | 32.0 | 67.6 |
| 11 | | 10 | 5.0 KOH | 87–100 | 2.5 | 63.0 | 76.2 | 18.6 | 79.7 |
| 12 | | 10 | 1.0 KOH | 30–35 60 | 46 6 | 37.7 | 61.6 | 52.1 46.1 | 45.2 52.9 |
| 13 | 6-methyl-5-heptene-2-one ↓ 3,7-dimethyl-2,6-octadiene nitrile | 10 | 0.1 KOH | 83 | 25 | 56.5 | 63.6 | 13.6 | 80.9 |
| 14 | ◯=O → ◯=CHCN | 10 | 1.0 KOH | 79 | 15 | 19.4 | 19.5 | 2.1 | 97.9 |
| 15 | 4,7-Dimethyl-6-octen-3-one ↓ 3-Ethyl-4,7-dimethyl-2,6-octadiene nitrile | 10 | 1.0 KOH | 83–119 | 112 | 34.1 | 36.6 | 13.9 | 58.8 |
| 16 | 2,7-Dimethyl-6-octen-3-one ↓ 7-methyl-3-isopropyl-2,6-nonadiene nitrile | 10 | 1.0 KOH | 84–109 | 88 | 42.7 | 67.5 | 43.6 | 51.1 |
| 17 | 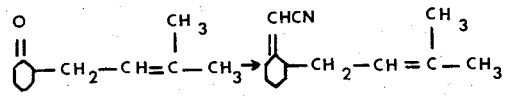 | 10 | 1.0 KOH | 84–90 | 17.5 | 44.6 | 44.6 | 0.0 | 74.3 |
| 18 | 3,6-Dimethyl-5-hepten-2-one ↓ 3,4,7-Trimethyl-2,6-octadiene nitrile | 1 | 0.1 KOH | 128–139 | 46 | 21.8 | 50.7 | 69.4 | 30.5 |

TABLE I-continued

| Ex. No. | Ketone and Nitrile | Moles per mole of Ketone | | Temp °C | Time Hr | Direct Yield | True Yield | ←Relative %[4] by glc → | |
|---|---|---|---|---|---|---|---|---|---|
| | | Aceto-nitrile | Catalyst | | | | | % starting ketone | % nitrile |
| 19 | and 7-Methyl-6-octen-3-one ↓ 3-Ethyl-7-methyl-2,6-octadiene nitrile | 10 | 0.1 NaOH[1] | 84–105 | 0.6 | 47 | 54.4 | 19.6 | 80.4 |
| 20 | | 50 | 1.0 KOH | 84 | 24 | 70.3 | 96.4 | 22.6 | 77.4 |
| 21 | 6-methyl-5-hepten-2-one ↓ 3,7-dimethyl-2,6-octadiene nitrile | 10 | 1.0 NaOH[1] | 27–30 50–65 | 22 1 | 28.4 | 31 | 51.8 20.2 | 48.2 79.8 |
| 22 | 3,6-Dimethyl-5-hepten-2-one ↓ 3,4,7-Trimethyl-2,6-octadiene nitrile and | 10 | 1.0 NaOH[2] | 50–55 85–88 | 16 8 | 51.7 | 64.5 | 27.5 | 72.5 |
| 23 | 7-Methyl-6-octen-3-one ↓ 3-Ethyl-7-methyl-2,6-octadiene nitrile | 10 | choline[5] base 45% in Methanol | 73 76 | | 20.4 | 77.6 | 75.4 | 29.2 |

[1]Dimethyl sulfoxide, 780 g./mol ketone
[2]m-pyrrole, 1000 g./mol ketone
[3]methyl alcohol, 324 g./mol ketone
[4]gas - liquid chromatography
[5]Choline base [(CH₃)₃ (CH₃CH₂OH)N] OH

EXAMPLES 24 to 28

A mixture of 12.6 g of 6-methyl-5-hepten-2-one, 0.1 mole, 41 g of acetonitrile, 1 mole, and 0.55 g of potassium hydroxide 0.01 mole was placed in a glass pressure vessel into which was placed a Teflon-coated magnetic stirring bar. The vessel was then closed. The reaction mixture was heated at 105° to 114°C. with stirring for 2 hours, and then cooled.

The reaction mixture was then stirred into 125 ml of aqueous acetic acid to neutralize the base, and 25 ml of benzene was added to the resulting mixture. The benzene phase was separated from the aqueous phase, and washed twice with 10 ml of 10% hydrochloric acid. The aqueous phase was then re-extracted three times in succession with 15 ml portions of benzene.

The benzene phases were combined, and the benzene removed under aspirator vacuum. The residual oil was distilled at from 4.5 to 0.8 mm Hg under a head temperature of from 80° to 95°C. to a pot temperature of 94° to 164°C. In this manner, there was recovered 1.4 g of unreacted methyl heptenone and 6.8 g of geranonitrile.

Following the above procedure, the ketones set forth in Table II were also reacted, under the conditions set forth in the Table:

TABLE II

| Example No. | Ketone and Nitrile | Moles per mole of Ketone | | Temp °C | Time Hr | Direct Yield | True Yield | ←Relative %[4] glc → | |
|---|---|---|---|---|---|---|---|---|---|
| | | Aceto-nitrile | Catalyst | | | | | % starting ketone | % nitrile |
| 24 | 3,6-Dimethyl-5-hepten-2-one ↓ 3,4,7-Trimethyl-2,6-octadiene nitrile | 10 | 0.1 KOH | 106–114 | 7.75 | 61.2 | 69.4 | 13.0 | 79.1 |
| 25 | | 10 | 0.1 NaOH[6] | 108–114 | 8.75 | not worked up | | 89.9 | 10.1 |
| 26 | and 7-Methyl-6-octen-3-one ↓ 3-Ethyl-7-methyl-2,6-octadiene nitrile | 10 | 0.1 KOtBu | 105 | 11.5 | 54.9 | 76.8 | 30.7 | 69.3 |
| 27 | | 10 | 0.1 KOH | 148–150 | 4.5 | 49.8 | 63.6 | 26.4 | 73.6 |
| 28 | | 10 | 1.0 Ba(OH)₂[5] | 105 124 | 53.71 | 15.2 | 44.0 | 78.2 | 20 |

[4]gas - liquid chromatography
[5]780 g. dimethyl sulfoxide/ mol ketone
[6]36 g. MeOH/ mol ketone

EXAMPLES 29 to 32

A mixture of cyclohexanone, acetonitrile, base, as noted in the Table, and the solvent if present, noted in the Table, was heated to reflux at 84°C. with mechanical stirring under a static nitrogen head for the time noted in the Table. After cooling, the reaction mixture was stirred into acetic acid to neutralize the base. The mixture was then shaken and the benzene phase separated if benzene was present as a solvent. If no benzene solvent was present, benzene was added, the mixture shaken, and the benzene phase separated.

The benzene phase was washed twice with 10% hydrochloric acid and the aqueous phases reextracted three times with benzene.

The benzene phases were combined and the benzene removed under aspirater vacuum. Distillation of the residual oil was carried out at 4.5 to 0.8 millimeters mercury under a head temperature of from 80° to 95°C. and a pot temperature of from 94° to 164°C.

Using this procedure and the bases and solvents indicated in the Table, the following results were obtained:

TABLE III

| Example No. | Ketone and Nitrile | Moles per mole of Ketone Acetonitrile | Catalyst | Temp °C | Time Hr | Direct Yield | True Yield | ←Relative %[a] by glc → % starting ketone | % nitrile |
|---|---|---|---|---|---|---|---|---|---|
| 29 | | 2 | 0.02 KOH 200 g. benzene | 81–83 | 47 | 39.6 | 56.3 | 35.2 | 57.2 |
| 30 | ⬡=O → ⬡=CHCN | 2 | 0.02 KOH | 79–82 | 42 | 13.4 | 34.2 | 74.6 | 20.1 |
| 31 | | 2 | 0.02 KOMe 240 g. benzene | 82 | 16 | 48.8 | 56.3 | 11.6 | 67.8 |
| 32 | | 2 | 0.1 KOH 176 g. benzene | 80–83.5 | 20 | 41.8 | 63 | | |

[a]gas - liquid chromatography

The α, β-unsaturated nitriles of the invention are useful components of perfume compositions, and may be used alone in such compositions or blended with other organic compounds, including, for example, alcohols, aldehydes, ketones, esters, and hydrocarbons, which are combined in proportions selected so that the combined odors of the individual compounds produce a pleasant fragrance. Such perfume compositions may be used alone or may be blended into soaps, detergents, space sprays, cosmetics, depilatories, permanent hair wave and hair rinse compositions.

In perfume compositions, each individual component will contribute its particular olfactory characteristic, but the overall effect will be the sum of each ingredient. The α, β-unsaturated nitriles of the invention can be used to alter the aroma characteristics of a perfume composition by highlighting or moderating the olfactory reaction contributed by the other ingredients in the composition.

The following Examples illustrate preferred embodiments of perfume mixtures, soap, detergent, and cosmetic powder compositions containing the α, β-unsaturated nitriles produced in accordance with the process of the invention.

EXAMPLE 33

Preparation of soap compositions

A total of 100 grams of soap chips are mixed with one gram of each of the perfume compositions given below until a substantially homogeneous composition is obtained. Both soap compositions manifest a characteristic lemon-like odor with the composition containing the mixture from Example 1 having the more delicate aroma at some sacrifice in strength.

The perfume compositions consist of the following ingredients in the parts by weight indicated:

| | |
|---|---|
| Geranium bourbon | 175 |
| Citronellol | 150 |
| Geraniol | 100 |
| Phenyl ethyl alcohol | 90 |
| Amyl cinnamic aldehyde | 200 |
| Cyclamal | 20 |
| 4-(4-methyl, 4-hydroxy amyl)-3-cyclohexene carboxaldehyde | 100 |
| Tetrahydro linalool | 37.5 |
| Tetrahydro myrcenol | 37.5 |
| Linalool | 75 |
| Citronellyl acetate | 125 |
| Phenyl ethyl acetate | 5 |
| Phenyl acetaldehyde dimethyl acetal | 10 |
| Cinnamic alcohol | 35 |
| Terpineol | 100 |
| Linalyl acetate | 25 |
| Musk ketone | 10 |
| Indole | 10 |
| Mixture from Examples 1 or 2 | 10 |

EXAMPLE 34

Preparation of detergent composition

A total of 100 grams of a detergent powder are mixed with a 0.15 gram of a perfume composition containing the mixture obtained in Example 1 until a substantially homogeneous composition having a lemon-like odor is obtained.

The perfume composition consisted of the following ingredients in parts by weight indicated:

| | |
|---|---|
| Decyl aldehyde, 10% solution in diethyl phthalate | 4 |
| Terpinyl acetate | 100 |
| Terpineol | 40 |
| Linalool acetate | 100 |
| Orange oil | 350 |
| Geranyl acetate | 100 |
| Geraniol | 35 |
| Coumarin | 2 |
| Mixture of Example 1 | 70 |

EXAMPLE 35

Preparation of cosmetic powder composition

A cosmetic powder is prepared by mixing 100 grams of talcum powder with 0.25 gram of the mixture obtained in Example 1 in a ball mill. The powder has a lemon-like odor.

EXAMPLE 36

Liquid detergent containing 7-methyl-3-methylene-6-octenenitrile

Concentrated liquid detergents with a lemon-like odor are prepared containing 0.1, 0.2 and 0.5 percent of the mixture of Example 1.

The amount of mixtures or compounds of this invention which will be effective in perfume compositions depends on many factors, including the other ingredients, their amounts and the effects which are desired. It has been found that perfume compositions containing as little as 0.02% by weight of mixtures or compounds of the invention, or even less may be usefully employed. For certain compositions as much as 5% by weight or even higher is useful. When used in soaps and other products the amount of perfume composition is the same as in generally employed with ordinary compositions, i.e. from about 1 to about 3% by weight.

Thus, as little as 0.0002% by weight of a product or mixture of products of this invention may be used to impart a lemon-like odor to soaps, cosmetics and other products.

Having regard to the foregoing disclosure, the following is claimed as the inventive and patentable embodiments thereof:

1. A process for preparing α, β-unsaturated nitriles having the formula:

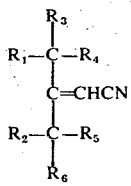

which comprises reacting an aliphatic ketone having the formula:

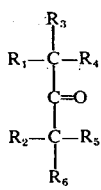

wherein $R_1$ and $R_2$ are selected from the group consisting of hydrogen and alkyl and alkenyl groups having from one to about 20 carbon atoms, and $R_3$, $R_4$, $R_5$, and $R_6$ are selected from the group consisting of hydrogen and alkyl groups having from one to about 20 carbon atoms, with acetonitrile at a temperature within the range from about 20° to about 200°C in the presence of a strong base selected from the group consisting of alkali metal hydroxides, barium hydroxide, and quaternary ammonium hydroxides having the formula:

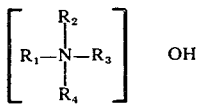 OH wherein $R_1$, $R_2$, $R_3$, and $R_4$ are organic radicals having from one to about thirty carbon atoms and selected from the group consisting of alkyl, hydroxyalkyl, cycloalkyl, aryl, and aryl substituted with alkyl, hydroxyalkyl and halogen, thereby inserting a =CHCN group at the keto carbon atom of the ketone, displacing the oxygen atom, with the formation of an unsaturated bond at the α, β-position between the methylene carbon of the acetonitrile and the keto carbon of the ketone.

2. A process according to claim 1 in which one of $R_1$ and $R_2$ is alkenyl and the other is alkyl.

3. A process according to claim 1 in which one of $R_1$ and $R_2$ is alkenyl and the other is hydrogen.

4. A process according to claim 1 in which a saturated ketone is used, and the reaction product is a monoethylenically α, β-unsaturated nitrile.

5. A process according to claim 1 in which an unsaturated monoethylenic ketone is used, and the reaction product is a dienic α, β-unsaturated nitrile.

6. A process according to claim 1 in which the nitrile reaction product is conjugated.

7. A process according to claim 1 in which the starting ketone is methylheptenone and the nitrile reaction product is geranonitrile.

8. A process according to claim 1 in which excess acetonitrile is used, and serves also as a solvent for the ketone reaction mixture.

9. A process according to claim 1 in which the base is an alkali metal hydroxide.

10. A process according to claim 1 in which the base is a barium hydroxide.

11. A process according to claim 1 in which the amount of base is within the range from about 0.01 to about 10 moles per mole of ketone.

12. A process according to claim 1 in which an organic solvent is included in the reaction mixture.

13. A process according to claim 1 in which the reaction temperature is within the range from about 50°C to about 125°C.

14. A process according to claim 1 in which at the completion of the reaction, the reaction mixture is neutralized with acid, forming an aqueous phase, the reaction product is dissolved in an organic solvent for the reaction product which is not miscible with the aqueous phase, and the aqueous phase is separated from the organic phase containing the reaction product.

15. A process for preparing α, β-unsaturated nitriles having the formula:

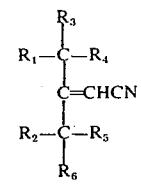

which comprises reacting an aliphatic ketone having the formula:

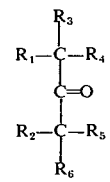

wherein $R_1$ and $R_2$ are selected from the group consisting of hydrogen and alkyl and alkenyl groups having from one to about twenty carbon atoms, and $R_3$, $R_4$, $R_5$, and $R_6$ are selected from the group consisting of hydrogen and alkyl groups having from one to about twenty carbon atoms, with acetonitrile in a closed reactor or under reflux at a temperature within the range from about 20° to about 200°C in the presence of a strong base selected from the group consisting of alkali metal hydroxides, barium hydroxide, alkali metal lower alkyl alcoholates having from one to four carbon atoms in the alkyl, and quaternary ammonium hydroxides having the formula:

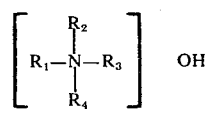 OH wherein $R_1$, $R_2$, $R_3$, and $R_4$ are organic radicals having from one to about thirty carbon atoms and selected from the group consisting of alkyl, hydroxyalkyl, cycloalkyl, aryl, and aryl substituted with alkyl, hydroxyalkyl and halogen, thereby inserting a =CHCN group at the keto carbon atom of the ketone, displacing the oxygen atom, with the formation of an unsaturated bond at the $\alpha$, $\beta$-position between the methylene carbon of the acetonitrile and the keto carbon of the ketone.

16. A process according to claim 15 in which one of $R_1$ and $R_2$ is alkenyl and the other is alkyl.

17. A process according to claim 15 in which one of $R_1$ and $R_2$ is alkenyl and the other is hydrogen.

18. A process according to claim 15 in which a saturated ketone is used, and the reaction product is a monoethylenically $\alpha$, $\beta$-unsaturated nitrile.

19. A process according to claim 15 in which an unsaturated monoethylenic ketone is used, and the reaction product is a dienic $\alpha$, $\beta$-unsaturated nitrile.

20. A process according to claim 15 in which the nitrile reaction product is conjugated.

21. A process according to claim 15 in which the starting ketone is methylheptenone and the nitrile reaction product is geranonitrile.

22. A process according to claim 15 in which excess acetonitrile is used, and serves also as a solvent for the ketone reaction mixture.

23. A process according to claim 15 in which the base is an alkali metal hydroxide.

24. A process according to claim 15 in which the base is an alkali metal alkoxide of a lower aliphatic alcohol having from one to about four carbon atoms.

25. A process according to claim 15 in which the amount of base is within the range from about 0.01 to about 10 moles per mole of ketone.

26. A process according to claim 15 in which an organic solvent is included in the reaction mixture.

27. A process according to claim 15 in which the reaction temperature is within the range from about 50°C to about 125°C.

28. A process according to claim 15 in which at the completion of the reaction, the reaction mixture is neutralized with acid, forming an aqueous phase, the reaction product is dissolved in an organic solvent for the reaction product which is not miscible with the aqueous phase, and the aqueous phase is separated from the organic phase containing the reaction product.

* * * * *

PO-1050 (5/69)

UNITED STATES PATENT OFFICE
CERTIFICATE OF CORRECTION

Patent No. 3,960,923      Dated   June 1, 1976

Inventor(s)   Robert S. DeSimone

It is certified that error appears in the above-identified patent and that said Letters Patent are hereby corrected as shown below:

Column 2, line 6, "produce" should be -- product --.

Column 6, line 50, "seperate" should be -- separate --.

Column 7, line 6, "stability" should be -- oriental --.

Signed and Sealed this

First Day of March 1977

[SEAL]

Attest:

RUTH C. MASON
Attesting Officer

C. MARSHALL DANN
Commissioner of Patents and Trademarks

UNITED STATES PATENT OFFICE
CERTIFICATE OF CORRECTION

Patent No. 3,960,923     Dated June 1, 1976

Inventor(s) Robert S. DeSimone

It is certified that error appears in the above-identified patent and that said Letters Patent are hereby corrected as shown below:

Column 13, line 54, "unsatured" should be --unsaturated --.

Signed and Sealed this

Eighth Day of November 1977

[SEAL]

Attest:

RUTH C. MASON
*Attesting Officer*

LUTRELLE F. PARKER
*Acting Commissioner of Patents and Trademarks*